(12) United States Patent
Yamashita

(10) Patent No.: US 10,231,690 B2
(45) Date of Patent: Mar. 19, 2019

(54) X-RAY IMAGING DEVICE

(71) Applicant: SHIMADZU CORPORATION, Nakagyo-Ku, Kyoto-Shi, Kyoto (JP)

(72) Inventor: Noboru Yamashita, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/039,990

(22) PCT Filed: Nov. 29, 2013

(86) PCT No.: PCT/JP2013/082234
§ 371 (c)(1),
(2) Date: May 27, 2016

(87) PCT Pub. No.: WO2015/079570
PCT Pub. Date: Jun. 4, 2015

(65) Prior Publication Data
US 2016/0374642 A1 Dec. 29, 2016

(51) Int. Cl.
A61B 6/00 (2006.01)
A61B 6/08 (2006.01)
A61B 6/06 (2006.01)

(52) U.S. Cl.
CPC ............ *A61B 6/589* (2013.01); *A61B 6/08* (2013.01); *A61B 6/4464* (2013.01); *A61B 6/06* (2013.01)

(58) Field of Classification Search
CPC .. A61B 6/08; A61B 6/589; A61B 6/06; A61B 6/4464
See application file for complete search history.

(56) References Cited

U.S. PATENT DOCUMENTS

| 3,790,803 A * | 2/1974 | Phillips | A61B 6/14 378/170 |
| 4,017,737 A * | 4/1977 | Hudson | A61B 6/0457 378/20 |
| 2005/0264434 A1* | 12/2005 | Grunau | A61B 6/4464 341/8 |
| 2011/0186741 A1* | 8/2011 | Ohta | G01T 1/24 250/370.08 |
| 2015/0030135 A1* | 1/2015 | Choi | A61B 6/4405 378/189 |

FOREIGN PATENT DOCUMENTS

| JP | 01-042004 | 12/1989 |
| JP | 03-295540 | 12/1991 |
| JP | 3177838 | 7/2012 |

OTHER PUBLICATIONS

PCT/JP2013/082234 International Search Report dated Jan. 21, 2014, 3 pages—Japanese, 1 page—English.

* cited by examiner

Primary Examiner — Chih-Cheng Kao
(74) Attorney, Agent, or Firm — Andrew F. Young, Esq.; Lackenbach Siegel, LLP

(57) ABSTRACT

The X-ray imaging device includes an irradiation unit which includes an X-ray tube and a collimator; and a tape measure which has a scale band on which distances from the irradiation unit are printed so as to increase from one end to the other and a winding mechanism that holds and winds the other end of the scale band. The irradiation unit has a scale band fixing portion which fixes one end of the scale band, and a winding mechanism fixing portion which fixes the winding mechanism.

9 Claims, 4 Drawing Sheets (MODIFICATION)

X-RAY IMAGING DEVICE

CROSS REFERENCE TO RELATED APPLICATIONS

This application relates to and claims priority from Ser. No.: PCT/JP2013/082234 filed Nov. 29, 2013, the entire contents of which are incorporated by reference.

FIGURE SELECTED FOR PUBLICATION

FIG. 2

BACKGROUND OF THE INVENTION

Field of the Invention

The present invention relates to an X-ray imaging apparatus, and more particularly, relates to an X-ray imaging apparatus including a tape measure configured to measure a distance from an X-ray irradiation element.

Description of the Related Art

Conventionally, it is known that there is an X-ray imaging apparatus including a tape measure configured to measure a distance from an X-ray irradiation element. Such an X-ray imaging apparatus is disclosed in Japanese Utility Model Registration No. 3177838, for example.

The X-ray imaging apparatus disclosed in the aforementioned Japanese Utility Model Registration No. 3177838 is a medical X-ray imaging apparatus that includes an irradiation element including an X-ray tube to irradiate an X-ray to a subject and a collimator having a tape measure mounted in the outer side surface of the collimator per se. During X-ray imaging, a variety of distances including such as a distance from the focal position of the X-ray tube to the body surface of a target object (subject), a distance from the focal position of the X-ray tube to a target site (site for the X-ray imaging) of the subject, and a distance from the focal position of the X-ray tube to a surface of an X-ray detector, is measured by using the tape measure. The distance to the body surface of the object (subject) is used to set up the X-ray imaging condition including an X-ray irradiation duration and a tube current value and so forth, and the distance to the target site and the distance to the surface of the X-ray detector therefrom are used to calculate such as the magnification percentage of the X-ray image to be imaged. Depending on the structure of the X-ray imaging apparatus, a distance from the collimator to the subject (or the X-ray detector) may be about 2 meters at the longest, in case.

PRIOR ART DOCUMENTS

Patent Document 1: JP Utility Model Patent Registration No. 3177838 B1

ASPECTS AND SUMMARY OF THE INVENTION

Objects to be Solved

In the X-ray imaging apparatus according to the aforementioned Japanese Utility Model Patent Registration No. 3177838, when the tape of the tape measure mounted on the collimator is pulled out to measure the distance, the true-zero point of the tape is the tip of the pulled-out tape (i.e., in the hand) while the mark to be read off is positioned near the housing, a main body, of the tape measure (the collimator side). Thus, it is a problem that it is difficult for the operator to read off the mark, a measurement value, because of faraway position to be read off by the operator.

On the other hand, when the tip, true-zero, of the tape is fixed to the collimator and the main body of the tape measure is attachable to and detachable from the collimator, the operator can read the mark to get measurement value of the distance by holding the detached the main body of the tape measure from the collimator after moved to a target site to be measured. However, according to such a structure, the main body of the tape measure may not return to the collimator due to the own weight thereof or the tape measure per se may spring in random directions so that a dangerous situation may take place even when the operator hands off the main body of the tape measure after the measurement was over. Therefore, it is a problem that the operator must return again to the collimator to re-fix the main body of the tape measure.

There are some apparatuses provided with an ultrasonic distance meter or a laser distance meter in order to solve the above problems, but such apparatuses may not provide an accurate measurement due to reflection caused by a variety of extraneous objects and so forth, so that a tape measure that can measure absolutely the distance is still desperately needed.

The present invention has been proposed in order to solve the aforementioned problems and an object of the present invention is to provide an X-ray imaging apparatus that can easily and absolutely measure the distance.

Means for Solving the Problem

In order to attain the aforementioned object, an X-ray imaging apparatus according to an aspect of the present invention comprises an irradiation element including an X-ray tube and a collimator and a tape measure including a tape on which marks incremented from the one side toward the other side to provide a distance from the irradiation element are printed and a winding mechanism that can wind the tape while holding the other side of the tape, wherein the irradiation element includes a tape fixing element that fixes the one side of the tape and a winding mechanism fixing element that fixes the winding mechanism.

In the X-ray imaging apparatus according to one aspect of the present invention, as hereinabove described, the tape fixing element that fixes the one side of the tape and the winding mechanism fixing element that fixes the winding mechanism are provided in the irradiation element so that an operator can measure the distance in the middle position of the pulled-out tape, which is between the one end fixed to the tape fixing element and the other end held by the winding mechanism, by pulling out the tape. In this case, the one side having the true-zero point of the tape is fixed to the irradiation element (tape fixing element) and a mark position to be read off is in place near the hand of the operator so that the operator can easily read off the mark indicating a measurement value by the operator per se. Furthermore, the tape can be pulled out to the exact position for measurement so that the distance can be absolutely measured without influence of reflection by an extraneous object or the like that may take place when an ultrasonic method or a laser method is used. Thus, the distance can be easily and absolutely measured. In addition, the winding mechanism can remain fixed to the irradiation element (winding mechanism fixing element) so that the tape can be automatically re-housed in the winding mechanism when the operator releases the own hand from the pulled-out tape. According to the present invention, therefore, the operator does not have to return again to the position of the irradiation element in order to fix a main body of the tape measure and that is different from the case in which the operator per se has to move with the main body of the tape measure.

Preferably, the aforementioned X-ray imaging apparatus according to this aspect further comprises a folding member that engages with the tape to fold the tape, and the folding member has a structure of engaging with the tape such that a position of a folded portion of the tape shifts according to a pulled-out length of the tape when the tape is pulled out from the winding mechanism. According to such structure, the middle position between the one end of the tape (tape fixing element) and the other end of the tape (winding mechanism) can be folded by the folding member so that the operator can easily pull out the folded portion of the tape to the measurement target (the subject or the X-ray detector) just by gripping and pulling out the folding member.

Preferably, in such case, if the folding member includes an insertion engagement element through which the tape passes and is configured to fold the tape inserted into the insertion engagement element in the opposite direction, for example, the engagement state is prevented from release unlike the case in which the folding member is hooked over (engages with) the folded portion of the tape so that the tape can be held while ensuring an engagement state with the tape in accordance with the simple structure.

Preferably, in the aforementioned structure comprising the folding member, the folding member is configured to fold the tape at the position on the one end of the folding member and include a grip element by which the operator can grip the folding member by the own hand to the position of the other end. According to such structure, the operator can easily pull out the folding member to the measurement target (the subject or the X-ray detector) and the tape on the one end of the folding member is not covered by the hand of the operator even in the state in which the operator is gripping the grip element on the other end of the folding member so that the operator can absolutely read off the mark of the tape indicating the measurement value.

Preferably, in such case, the grip element includes a finger insertion element into which the operator inserts the own finger. According to such structure, the operator can insert the own finger into the finger insertion element to grip the folding member so that the operator can easily and assuredly grip and pull out the folding member even if the grip element is downsized Preferably, in the aforementioned structure comprising the folding member, the folding member includes a read-off position marking element that indicates the mark read-off position of the folded tape. According to such structure, the mark indicating the measurement value can be accurately read off at the mark read-off position indicated by the read-off position marking element without variation of the mark read-off position.

Preferably, in such case, the tape is fixed to the tape fixing element in a mark position at which a position of an true-zero point of the tape is offset by a distance between the mark read-off position of the read-off position marking element and the tip position of the folding member. According to such structure, the operator can obtain the distance to the tip position of the folding member just by reading a measurement value at the mark read-off position of the read-off position marking element. Therefore, the operator only needs to contact the tip of the pulled-out folding member to the measurement target (the subject, for example) and read off the mark as the measurement value indicated by the read-off position marking element so that the distance measurement can be further facilitated.

Preferably, in the aforementioned X-ray imaging apparatus according to the above one aspect, the tape is fixed to the tape fixing element in a mark position at which the position of the true-zero point of the tape is offset facing the focal position by the distance between the position at which the tape fixing element is positioned and the focal position of the X-ray tube. According to such structure, the distance from the focal position of the X-ray tube to the measurement target (the subject or the X-ray detector) can be directly measured without adding the distance between the tape fixing element and the focal position of the X-ray tube to the measurement value. Here, the distance between the position at which the tape fixing element is positioned and the focal position of the X-ray tube may vary according to the structure of the X-ray imaging apparatus so that it is necessary to prepare a tape measure provided with a different offset mark every variation (product lineup) of the X-ray imaging apparatus when the offset mark is provided on the tape, for example. In contrast, the present invention can accommodate a plurality of variations as to the X-ray imaging apparatus just by shifting the mark position, fixed by the tape fixing element, corresponding to the distance between the tape fixing element and the focal position.

Preferably, in the aforementioned X-ray imaging apparatus according to the above one aspect, the tape fixing element includes a pair of clamp members that clamp the tape and a fastening member that fastens the clamping members. According to such structure, the tape can be fixed by such simple structure and fixation can be easily released to adjust the position at which the tape is fixed (the mark position fixed by the tape fixing element).

Effect of the Invention

As hereinabove described, according to the present invention, the distance can be easily and absolutely measured. *

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
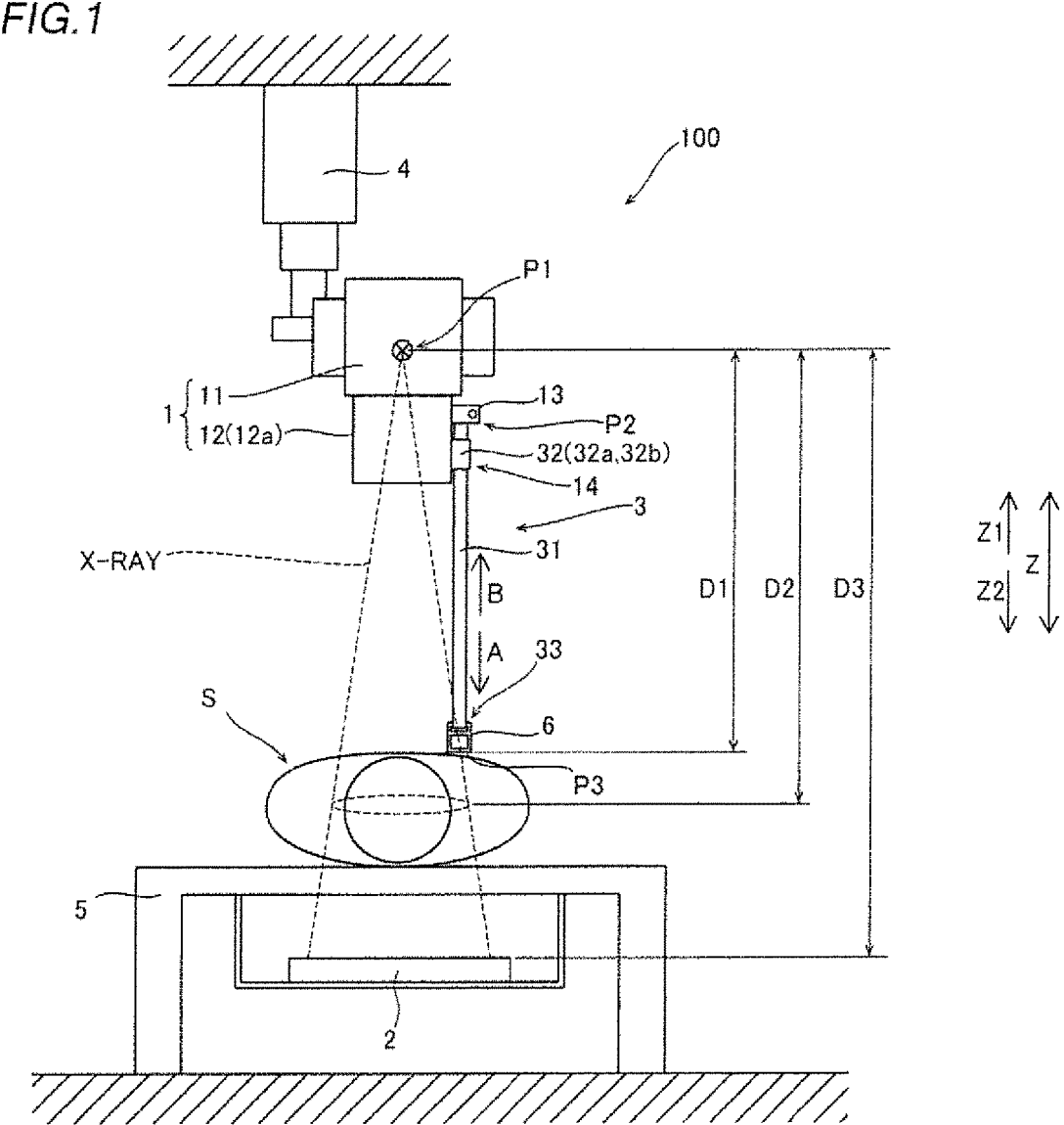
FIG. 1 is a schematic view showing the overall structure of an X-ray imaging apparatus according to the one aspect of the Embodiment of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

The aspect of the Embodiment of the present invention is hereinafter described on the basis of the drawings.

The overall structure of an X-ray imaging apparatus 100 according to the one aspect of the Embodiment of the present invention is now described with reference to FIGS. 1 to 5.

The X-ray imaging apparatus 100 according to the aspect of the Embodiment includes a ceiling-hung type irradiation element 1 supported by a support mechanism 4 and a detector 2 installed on an imaging platform 5 facing the irradiation element 1, as shown in FIG. 1. The X-ray imaging apparatus 100 further includes a tape measure 3, having a tape 31 and a main body 32 that winds and houses the tape 31, to measure the distance.

The X-ray imaging apparatus 100 is a medical X-ray imaging apparatus configured to image a subject S laid down on the imaging platform 5 by the irradiation element 1 and the detector 2 facing each other in the vertical direction. Specifically, the X-ray imaging apparatus 100 is configured to take an X-ray image by receiving X-ray, which is irradiated from the irradiation element 1 positioned above the imaging platform 5 and then transmitted through the subject S, by the detector 2. The detector 2 includes an FPD (flat panel detector), for example. The X-ray imaging apparatus 100 may be configured to image the upright subject S with the irradiation element 1 and the detector 2 facing each other in the horizontal direction.

The irradiation element 1 includes an X-ray tube 11 that generates X-ray and a collimator 12 installed on the front surface of the X-ray tube 11 in the X-ray irradiation direction (downward, here). The above tape measure 3 is installed in the irradiation element 1 and the irradiation element 1 includes a tape fixing element 13 that fixes the tape 31 of the tape measure 3 and a main body fixing element 14 that fixes the main body 32 of the tape measure 3. The main body fixing element 14 is an example of the "winding mechanism fixing element" of the present invention.

Figure 2:
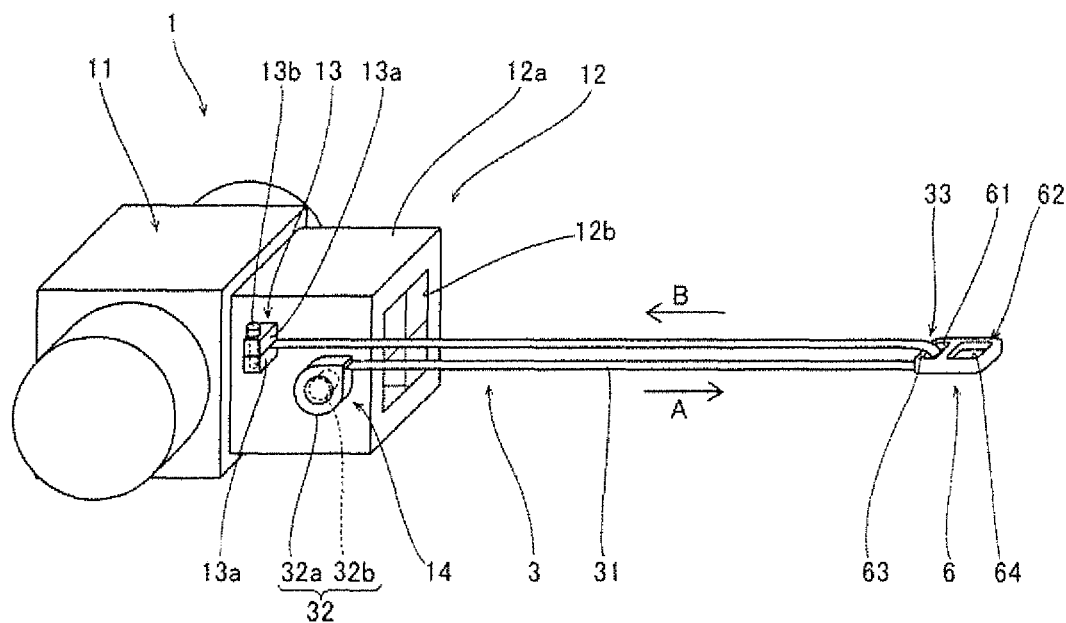
FIG. 2 is a perspective view schematically showing an irradiation element and a handle of the X-ray imaging apparatus according to the one aspect of the Embodiment of the present invention.

The X-ray tube 11 generates an X-ray by irradiating an electron beam from the cathode to the target anode. The X-ray generated by the X-ray tube 11 is emitted downward (toward the detector 2) in a radial fashion passing through a focal position P1. As shown in FIGS. 1 and 2, the collimator 12, a beam limiting device of X-ray (focusing device), limits the beam area of X-ray through the focusing mechanism, not shown in FIG., built in a rectangular type housing box 12a and passes the emitted X-ray through an opening 12b (see FIG. 2) in place in the front side thereof (facing down) in the irradiation direction.

The tape measure 3 is mounted on the lateral surface of the housing 12a of the collimator 12 as a part of the irradiation element 1. Specifically, the main body 32 of the tape measure 3 is mounted and fixed on the main body fixing element 14 positioned on the side surface of the housing 12a by a fixing means such as an holder or a fastener member, not shown in FIG. The tape 31, made of metal, resin or the like, includes a mark 31a (see FIG. 3) having the tip of the fixing side of the tape fixing element 13 as the true-zero point (0 mark), Specifically, marks indicating the distance (mark 31a, see FIG. 3) from the irradiation element 1 are printed on the tape 3, which increment from the one end (from the tape fixing element 13) to the other end (to the main body 32), as shown in FIG. 2. In addition, the main body 32 includes a case 32a that winds the tape 31 to house and a winding mechanism 32b holding the other end of the tape 31 winds the tape 31. The winding mechanism 32b is housed in the case 32a and the winding mechanism 32b is fixed to the main body fixing element 14 through the case 32a. In addition, the winding mechanism 32b is configured to pull and bias the tape 31 in the winding direction toward the inside of the case 32a by a winding means, for example, such as a flat spiral spring (not shown in FIG.) connected to the other end of the tape 31. The tape measure 3 is configured to automatically wind the tape 31 pulled out from the main body 32 by the bias force of the winding mechanism 32b.

As shown in FIG. 1, the tape measure 3 is installed to measure a variety of distances including a distance D1 from the focal position P1 of the X-ray tube 11 to the body surface of an object (subject S), a distance D2 from the focal position P1 to a target site (an expected site subject to an X-ray imaging) of the subject S, and a distance D3 from the focal position P1 to a surface (detection surface) of the detector 2. The distance D1 to the body surface of the subject S is used to set up the X-ray imaging condition including an X-ray irradiation duration and a tube current value supplied to the X-ray tube 11 and so forth, and the distance D2 to the target site and the distance D3 to the surface of the detector 2 therefrom are used to calculate such as the magnification percentage (D2/D3) of the X-ray image to be imaged.

As shown in FIG. 2, the one end of the tape 31 of the tape measure 3 is fixed by the tape fixing element 13 and the main body 32 that houses the other end of the tape 31 is fixed by the main body fixing element 14 so that the tape 31 of the tape measure 3 may have a folding portion 33 at any middle position between the tape fixing element 13 and the main body 32 (main body fixing element 14), which is folded from the pull-out direction A toward the opposite direction B thereof relative to the tape 31. According to the aspect of the present Embodiment, a handle 6 is equipped to fold the tape 31 at any folding portion 33. The folding portion 33 (with handle 6) is pulled out so that the tape 31 can perform a length measurement therefor. Thus, the tape measure 3 can be configured to have the tip, the true-zero point of the mark 31a, located in the side of the irradiation element 1 (collimator 12) and the read-off position of the mark 31a during measurement located in the side following the folding portion 33. The handle 6 is an example of the "folding member" of the present invention.

More specifically, after being pulled out in the direction A from the main body 32, the tape 31 is folded toward the opposite direction (direction B) between the main body 32 and the tip and the tip of the tape 31 is fixed by the tape fixing element 13 installed to the housing 12a of the collimator 12. The tape fixing element 13 includes a pair of columnar clamp members 13a that clamp the tape 31 and a fastening member 13b, such as a bolt, that fastens the clamp members 13a. The pair of clamp members 13a clamp the tape 31 by fastening the fastening member 13b in the state in which the tape 31 is positioned between the pair of clamp members 13a so that the tape 31 can be fixed. Further, when the fastening member 13b is loosened to release fixation of the tape 31, the fixed position of the tape 31 can shift (be adjusted). The fixing position of the tape 31 is being discussed later.

Figure 3:
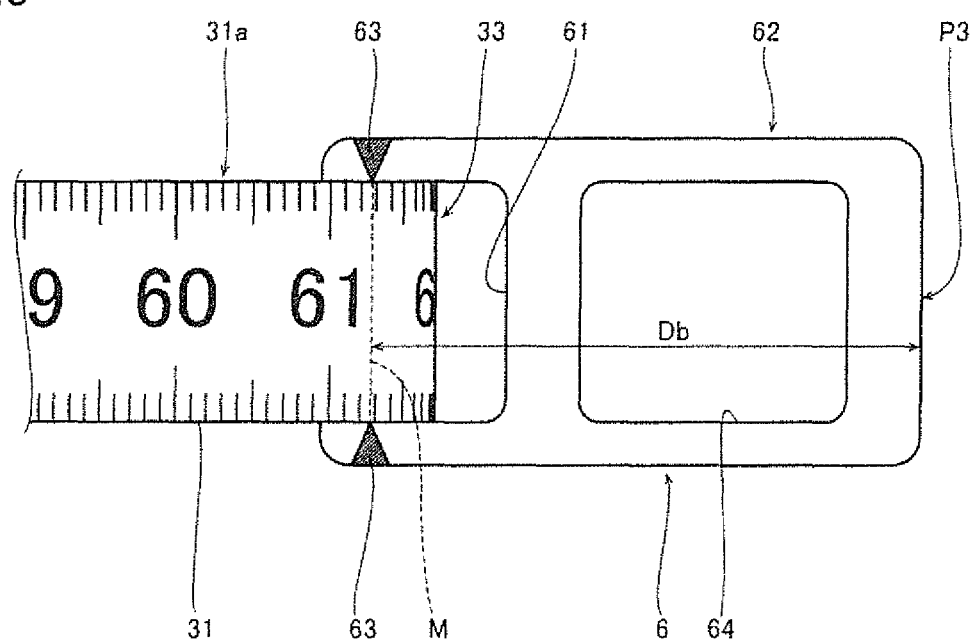
FIG. 3 is a plan view showing the handle and a tape of the X-ray imaging apparatus according to the one aspect of the present Embodiment of the present invention.
Figure 4:
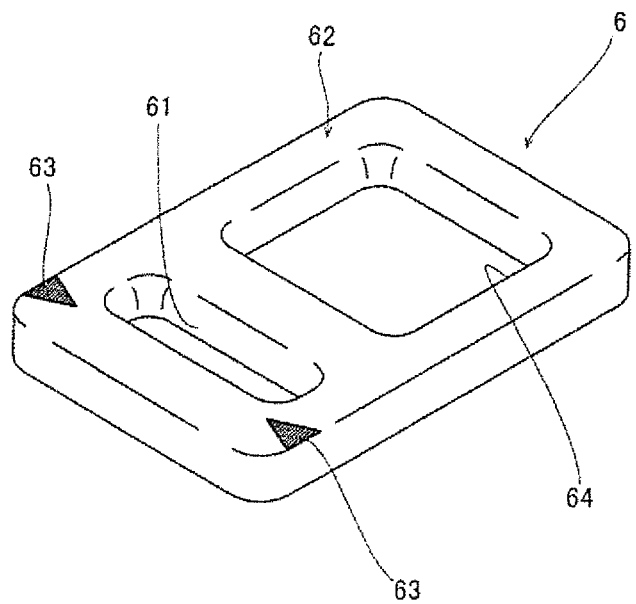
FIG. 4 is a perspective view schematically showing the handle of the X-ray imaging apparatus according to the one aspect of the Embodiment of the present invention.

The handle 6 made of resin or metal has a roughly rectangular type flat plate (having flat and thin shape with even thickness), as shown in FIGS. 2 to 4. The handle 6 engages with the tape 31 to fold the tape 31. The handle 6 has a structure capable of engaging with the tape 31 so that the position of the folded portion 33 can shift according to the pulled-out length of the tape 31 when the tape 31 is pulled out from the winding mechanism 32b. In the handle 6, an insertion engagement hole 61, through which the tape 31 can pass, a grip element 62 and read-off position marking elements 63 are integrally formed. The insertion engagement hole 61 is positioned on the one end (the side facing the irradiation element 1) of the handle 6 and the grip element 62 is positioned on the other end (the tip side facing the measurement target) of the handle 6. The read-off position marking elements 63 are positioned in a flat portion between the insertion engagement hole 61 and the one end of the handle 6. The insertion engagement hole 61 is an example of the "insertion engagement element" of the present invention.

The insertion engagement hole 61 is a through-hole having rounded corners and dimensioned corresponding to the width of the tape 31. The handle 6 is configured to fold the tape 31 inserted into the insertion engagement hole 61 toward the opposite direction. Specifically, as shown in FIG. 2, the tape 31 pulled out from the main body 3 is inserted into the insertion engagement hole 61 of the handle 6 from the rear side as in the direction A and taken out to the front side and then folded toward and fixed to the tape fixing element 13 of the collimator 12 as in the direction B. Due to such structure, when the handle 6 is gripped and pulled in the direction A, the tape 31 passing through the insertion engagement hole 61 can be pulled out from the main body 32 and the position of any folded portion 33 (handle 6) shifts in accordance with just the pulled-out length of the tape 31 in the direction A. The inner surface of the insertion engagement hole 61 (through-hole) is chamfered as rounded in order to reduce friction during the pull-out operation.

The grip element 62 on the other end of the handle 6 is installed so that an operator can grip the handle 6 by hand. As shown in FIGS. 3 and 4, the grip element 62 is formed as the finger(s) of the operator can be inserted into the insertion hole 64. The finger insertion hole 64 includes a through-hole having rounded corners and the operator inserts the finger(s) into the finger insertion hole 64 so that the finger(s) of the operator can be engaged with the handle 6. The inner surface of the finger insertion hole 64 (through-hole) is chamfered as round so that the operator can easily insert the finger (s) into the finger insertion hole 64. The finger insertion hole 64 is an example of the "finger insertion element" of the present invention.

The read-off position marking elements 63 have a marking function relative to the mark read-off position M of the folded tape 31, as shown in FIG. 3. The read-off position marking element 63 is positioned on the flat portion (see FIG. 4) corresponding to the width between the edge of insertion engagement hole 61 (through-hole) and the one end of the handle 6 and the pair thereof are marked both lateral sides on the flat surface relative to the tape 31. The read-off position marking elements 63 can be an arrow type (like triangle) mark installed on the top side of the handle 6, which can be formed by using a method including such as attaching a sticker, printing or engraving on the handle 6. The tape measure 3 is configured to provide the measurement value corresponding to the mark therefor matching to the mark read-off position M indicated by the read-off position marking elements 63 as the read-off position marking elements 63 is a marker.

Figure 5:
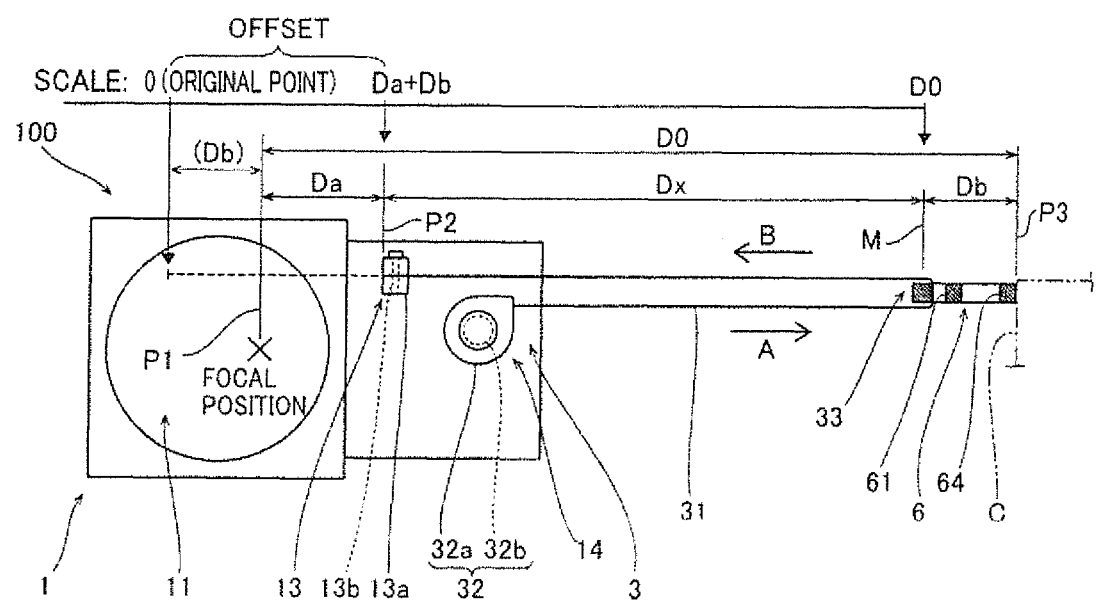
FIG. 5 is a schematic side view for illustrating a position where the tape is fixed in the X-ray imaging apparatus according to the one aspect of the Embodiment of the present invention.

Next, the position at which the tape 31 is fixed by the tape fixing element 13 is now described. According to the aspect of the present Embodiment, the tape 31 is fixed to the tape fixing element 13 in a mark position at which the position of the true-zero point of the tape 31 is offset toward the focal position P1 by the distance Da between the position P2 at which the tape fixing element 13 is positioned and the focal position P1 of the X-ray tube 11, as shown in FIG. 5. Furthermore, the tape 31 is fixed to the tape fixing element 13 in the mark position at which the position of the true-zero point of the tape 31 is further offset by the distance Db between the mark read-off position M of the read-off position marking elements 63 (see FIG. 3) and the tip (the other end) position P3 of the handle 6. Detailed description is provided below.

As shown in FIG. 1, the tape measure 3 is installed to measure a variety of distances D1, D2, and D3 from the focal position P1 of the X-ray tube 11. As shown in FIG. 5, the distance from the focal position P1 to a measurement target C (e.g., the body surface of the subject S in the case of measurement of the distance D1) is D0. The distance D0 can be configured based on the distance Da between the position P2, at which the tape fixing element 13 is positioned, and the focal position P1 of the X-ray tube 11; the distance Dx between the tape fixing element 13 and the mark read-off position M of the read-off position marking elements 63; and the distance Db between the mark read-off position M of the read-off position marking elements 63 and the tip (other end) position P3 of the handle 6.

The distance Da of the distances Da, Dx, and Db making the distance D0 is a fixed value determined by the focal position P1 of the X-ray tube 11 and the installation position P2 of the tape fixing element 13 based on the apparatus design The distance Db is a fixed value determined by the dimension of the handle 6 based on the apparatus design. Then, the actual measurement value variable depending on the tape 31 pulled out by pulling the handle 6 is the distance Dx. According to the aspect of the present Embodiment, the tape 31 fixed to the tape fixing element 13 is in the state in which the position of the true-zero point (mark 0 position) of the tape 31 is pre-shifted (offset) toward the focal position P1 by the distance Da and the distance Db. Specifically, the tape 31 is fixed to the tape fixing element 13 in the position at which the read-off value of the mark 31a (see FIG. 3) is (Da+Db). Consequently, if the mark 31a in the mark read-off position M (read-off position marking elements 63) is read off when the handle 6 (folded portion 33) is pulled by the distance Dx and the tip (the other end) of the handle 6 contacts the measurement target C, the obtained measurement value is the distance D0=(Da+Db) Dx.

Thus, the operator can obtain the distance D0, from the focal position P1 of the X-ray tube 11 to the measurement target C, as a measurement value just by inserting the finger into the finger insertion hole 64 of the handle 6, pulling the handle 6 (folded portion 33) and reading off the mark 31a in the mark read-off position M when the tip (the other end) of the handle 6 contacts to the measurement target C. Further, in practice, the distance Da based on the design value may vary according to the type of the X-ray imaging apparatus 100. Even in such a case, according to the aspect of the present Embodiment, the fixed position of the tape 31 clamped by the tape fixing element 13 is freely adjustable so that the tape 31 can be fixed to the tape fixing element 13 in the position having the offset value (read-off mark) according to the type of each apparatus. In addition, FIG. 5 illustrates the example in which the surplus tip portion (the portion shown by the broken lines in FIG. 5) is excluded after the tape 31 was fixed.

According to the aspect of the present Embodiment, the following advantageous effects can be obtained.

According to the aspect of the present Embodiment, as hereinabove described, the tape fixing element 13 that fixes the one end of the tape 31 and the main body fixing element 14 that fixes the winding mechanism 32b are installed in the irradiation element 1 so that the operator can measure the distance in the middle position (folded portion 33) between the one end of the tape 31 fixed to the tape fixing element 13 and the other end of the tape 31 held by the winding mechanism 32b by pulling out the tape 31 when measures the distance. In such case, the one end having the true-zero point of the tape 31 is fixed to the irradiation element 1 (tape fixing element 13) and the mark read-off position M is in place near the hand of the operator so that the operator can easily read off the mark indicating the measurement value by the operator per se. Furthermore, the tape 31 can be pulled to the measurement position so that the distance can be absolutely measured without influence of reflection by any extraneous object or the like that may take place when an ultrasonic method or a laser method is applied. Thus, the distance can be easily and absolutely measured. In addition, the winding mechanism 32b (main body 32) can remain fixed to the irradiation element 1 (main body fixing element 14) so that the tape 31 can be automatically re-housed into the winding mechanism 32b when the operator released the own hand from the pulled-out tape 31. Therefore, according to the present invention, the operator does not have to return again to the position of the irradiation element in order to fix the main body of the tape measure and that is different from the case in which the operator per se has to move with the main body of the tape measure.

In addition, according to the aspect of the present Embodiment, as hereinabove described, the handle 6 that folds the tape 31 is installed and the handle 6 has the structure of engaging with the tape 31 so that the position of the folded portion 33 can shift following the pulled-out length of the tape 31 when the tape 31 is pulled out from the winding mechanism 32b. Thus, the operator can easily pull out the folded portion 33 of the tape 31 to the measurement target C (the subject or an X-ray detector) just by gripping and pulling the handle 6.

In addition, according to the aspect of the present Embodiment, as hereinabove described, the insertion engagement hole 61 through which the tape 31 passes is installed in the handle 6 and the handle is configured to fold the tape 31 inserted into the insertion engagement hole 61 in the opposite direction B. Thus, disengagement between the handle 6 and the tape 31 is prevented so that the handle 6 can fold the tape 31 while ensuring the engagement with the tape 31 according to the simple structure.

In addition, according to the aspect of the present Embodiment, as hereinabove described, the handle 6 is configured to fold the tape 31 in a position on the one end (facing the irradiation element 1) of the handle 6, and the grip element 62, by which the operator can grip the handle 6 by hand, is installed in the position on the other end (facing the measurement target) of the handle 6. Thus, the operator can easily pull the handle 6 by the measurement target C (the subject S or the detector 2), and the tape 31 on the one end of the handle 6 is not covered by the hand of the operator even when the operator grips the grip element 62 on the other end of the handle 6 so that the operator can absolutely read off the mark on the tape 31 indicating the measurement value.

In addition, according to the aspect of the present Embodiment, as hereinabove described, the finger insertion hole 64, which the finger of the operator is inserted into, is installed in the grip element 62. Thus, the operator can insert the finger into the finger insertion hole 64 to grip the handle 6 so that the operator can easily and assuredly grip and pull the handle 6 even when the grip element 62 is downsized.

According to the aspect of the present Embodiment, as hereinabove described, the read-off position marking elements 63 that indicate the mark read-off position M of the tape 31 are installed in the handle 6. Thus, a measurement value can be accurately read off without variation of the mark read-off position M.

In addition, according to the aspect of the present Embodiment, as hereinabove described, the tape 31 is fixed to the tape fixing element 13 in the mark position at which the position of the true-zero point of the tape 31 is offset by the distance Db between the mark read-off position M and the tip position P3 of the handle 6. Thus, the operator can obtain the distance to the tip position P3 of the handle 6 therefrom just by reading off the mark as the measurement value at the mark read-off position M. Therefore, the operator only needs to contact the tip (tip position P3) of the pulled handle 6 to the measurement target C (the subject S, for example) and then read off the mark as the measurement value indicated by the read-off position marking elements 63 so that the distance measurement can be further facilitated.

In addition, according to the aspect of the present Embodiment, as hereinabove described, the tape 31 is fixed to the tape fixing element 13 in the mark position at which the position of the true-zero point of the tape 31 facing the focal position P1 is offset by the distance Da between the position P2, at which the tape fixing element 13 is positioned, and the focal position P1. Thus, the distance from the focal position P1 of the X-ray tube 11 to the measurement target C (subject or X-ray detector) can be directly measured without conducting the add calculation to obtain the distance Da between the tape fixing element 13 and the focal position P1 to the measurement value. Furthermore, the present invention can accommodate a plurality of variations of the X-ray imaging apparatus 100 just by shifting the mark position fixed by the tape fixing element 13 according to the distance Da between the tape fixing element 13 and the focal position P1.

In addition, according to the aspect of the present Embodiment, as hereinabove described, the tape fixing element 13 includes the pair of clamp members 13a that clamp the tape 31 and the fastening member 13b that fastens the clamp members 13a. Thus, the tape 31 can be fixed by using a simple structure and fixation thereof can be easily released so that the fixed position of the tape 31 (the mark position fixed by the tape fixing element 13) can be easily adjusted.

The embodiment disclosed here must be considered as illustrative in all aspects but restrictive. The scope of the present invention is specified by the scope of claims but by the above description of the aspect of the Embodiment, and all modifications within the meaning and the scope equivalent to the scope of claims are further included.

For example, the example of the imaging target is a human being (subject) in the aforementioned Embodiment, but the present invention is not restricted thereto. The present invention may be applied to an X-ray imaging apparatus that takes an X-ray image of any creature other than a human being as the imaging target.

While the example of imaging the laid-down subject has been shown in the aforementioned aspect of the Embodiment, the present invention is not restricted thereto. The present invention may be applied to an X-ray imaging apparatus configured to image the subject in a rising state (an upright position).

While the example of mounting the tape measure 3 on the outside (the outer surface of the housing 12a) of the collimator 12 has been illustrated in the aforementioned aspect of the Embodiment, the present invention is not restricted thereto. According to the present invention, the tape measure 3 can be built in the collimator 12 (housing 12a).

Figure 6:
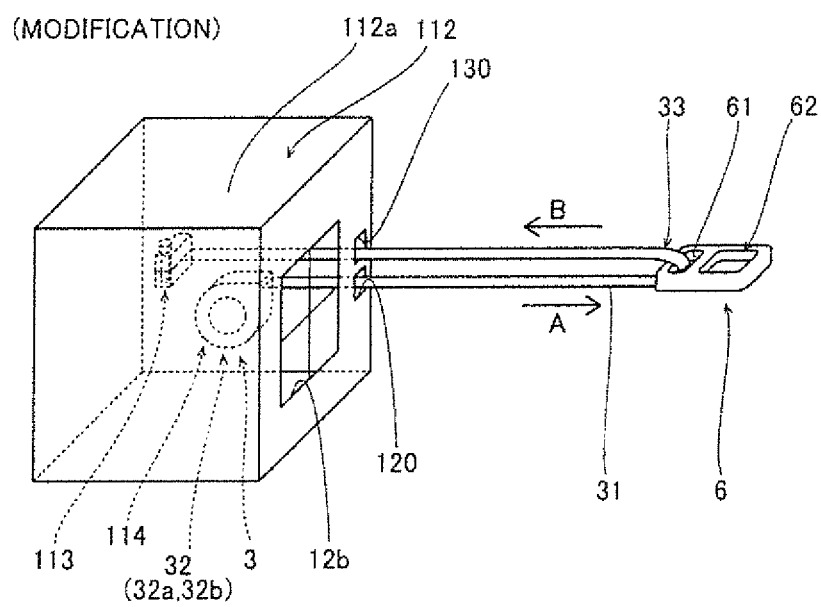
FIG. 6 is a perspective view schematically showing a modification of the irradiation element of the X-ray imaging apparatus according to the one aspect of the Embodiment of the present invention. *

Specifically, as the modification shown in FIG. 6, the tape measure 3 is mounted on the inside surface of the housing 112a of the collimator 112, and the opening 120, 130, which the tape 31 passes through, are formed in the front side in which the opening 12b of the collimator 112 is formed. The tape 31, passing through the hole 120, is pulled out from the main body 32 in the direction A and is folded to the direction B and then fixed to the tape fixing element 113 inside the housing 112a following passing through the hole 130. On the other hand, the main body 32 including the winding mechanism (not shown in FIG. 6) is fixed to the main body fixing element 114 on the inside surface of the housing 112a. The X-ray imaging apparatus is configured in such manner so that the tape measure 3 can be built in the collimator 112 (housing 112a). When the distances D1, D2, and D3 are measured, the closer to the irradiation axis of X-ray, the further improved measurement accuracy can be obtained so that such measurement accuracy can be easily improved by pulling out the tape 31 from the vicinity of the opening 12b that is the emission port of X-ray. Furthermore, the recess may be additionally formed on the front surface of the housing 112a so that the handle 6 can be stored in the recess.

In addition, according to the present invention, the tape measure may be mounted on the X-ray tube or the cover that covers the entire irradiation element including the collimator and the X-ray tube can be installed and then the tape measure can be mounted on the cover per se.

Further, according to the aspect of the aforementioned Embodiment, the tape fixing element 13 includes the clamp members 13a and the fastening member 13b but the present invention is not restricted thereto. According to the present invention, the tape fixing element may have a different structure. For example, a through-hole can be formed in the tape and the tape can be screwed to the tape fixing element having the screw hole or can be riveted to the tape fixing element.

In addition, according to the aspect of the aforementioned Embodiment, as an example of the insertion engagement element, the handle 6 having the engagement hole 61 including the through-hole is illustrated, but the present invention is not restricted thereto. The insertion engagement element according to the present invention can be a notch but the through-hole. For example, a slit can be formed on the one end of the handle 6 so as to connect to the insertion engagement hole 61 so that a notch-like insertion engagement element can be formed. Engagement between the handle 6 and the tape 31 can be obtained by forming a columnar engagement element in the handle 6 and engaging the columnar engagement element with the folded portion 33 rather than inserting the tape 31 into the insertion engagement hole 61.

Further, according to the aspect of the aforementioned Embodiment, as an example of the finger insertion element, the example having the finger insertion hole 64 including the through-hole is formed in the grip element 62 of the handle 6 is illustrated, but the present invention is not restricted thereto. According to the present invention, a finger insertion element including a (not through) recess instead of the finger insertion hole 64 including the through-hole can be installed. In addition, for example, a plate-like grip element is formed so that the operator can hold and grip the plate-like grip element. Furthermore, the grip element may not be formed in the handle.

In addition, according to the aspect of the aforementioned Embodiment, the example illustrates that the tape 31 is fixed in the state in which the position of the true-zero point of the tape 31 is offset by the distance Db between the mark read position M and the tip position P3 of the handle 6, but the present invention is not restricted thereto. According to the present invention, such offset by the distance Db is not mandatory.

Further, according to the aspect of the aforementioned Embodiment, the example illustrates that the tape 31 in the state in which the position of the true-zero point of the tape 31 facing the focal position P1 is offset by the distance Da between the position P2, at which the tape fixing element 13 is positioned, and the focal position P1, but the present invention is not restricted thereto. According to the present invention, such offset by the distance Da is not mandatory.

Further, according to the aspect of the aforementioned Embodiment, the example illustrates that the winding mechanism 32b is fixed to the main body fixing element 14 by fixedly mounting the main body 32 of the tape measure 3 on the main body fixing element 14, but the present invention is not restricted thereto. The main body fixing element can fix the winding mechanism (main body) as attachable and detachable rather than completely fixes the winding mechanism (main body). The main body fixing element can take any configuration so far as the mechanism capable of fixing the winding mechanism (main body) temporarily or permanently. For example, a case-like bracket is installed in the collimator 12 so that the main body 32 of the tape measure 3 can be housed in and taken out from the bracket. Furthermore, the winding mechanism 32b (main body 32) may simply be fixed by other fixing means including screwing and welding.

DESCRIPTION OF REFERENCE SIGNS

1 Irradiation element
3 Tape measure
6 Handle (folding member)
11 X-ray tube
12 Collimator
13, 113 Tape fixing element
13a Clamp member 13b Fastening member
14, 114 Main body fixing element (Winding mechanism fixing element)
31 Tape
32b Winding mechanism
33 Folded portion
61 Insertion engagement hole (Insertion engagement element)
62 Grip element
63 Read-off position marking element
64 Finger insertion hole (Finger insertion element)
100 X-ray imaging apparatus
P1 Focal position
P2 Position at which the tape fixing element is positioned
P3 Tip position of the handle
A Pull-out direction
B Opposite direction Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray imaging apparatus, comprising:
   an irradiation element including an X-ray tube and a collimator; and
   a tape measure system including a tape, on which a distance from said irradiation element is printed in an increment manner from a first end toward a second end of said tape, and a winding mechanism that holds the second ether end of said tape and winds said tape,
   wherein said irradiation element includes a tape fixing element that fixes the first end of said tape and a winding mechanism fixing element that fixes said winding mechanism.

2. The X-ray imaging apparatus according to claim 1, further comprising:
   a folding member that engages with said tape to fold said tape, and
   wherein said folding member has a structure engaging with said tape so that a position of a folded portion of said tape can shift according to a pulled-out length of said tape when said tape is pulled out from said winding mechanism.

3. The X-ray imaging apparatus according to claim 2, wherein:
   said folding member includes an insertion engagement element through which said tape passes and which folds said tape inserted into said insertion engagement element toward an opposite direction.

4. The X-ray imaging apparatus according to claim 2, wherein:
   said folding member is configured to fold said tape at a position on a first end of said folding member, and includes a grip element at a second end of said folding member that an external operator can grip by their own hand during a use.

5. The X-ray imaging apparatus according to claim 4, wherein:
   said grip element includes a finger insertion element shaped to receive a finger of said external operator during said use.

6. The X-ray imaging apparatus according to claim 2, wherein:
   said folding member includes a read-off position marking element that indicates a mark read-off position of said folded tape.

7. The X-ray imaging apparatus according to claim 6, wherein:
   said tape is fixed to said tape fixing element in a mark position at which a position of a true-zero point of said tape is offset by a distance between said mark read-off position of said read-off position marking element and a tip position of said folding member.

8. The X-ray imaging apparatus according to claim 1, wherein:
   said tape is fixed to said tape fixing element in a mark position at which a position of a true-zero point of said tape facing a focal position is offset by a distance between a position at which said tape fixing element is positioned and said focal position of said X-ray tube.

9. The X-ray imaging apparatus according to claim 1, wherein:
   said tape fixing element includes a pair of clamp members that clamp said tape and a fastening member that fastens said clamp members.

* * * * *